United States Patent [19]
Camu et al.

[11] Patent Number: 6,149,937
[45] Date of Patent: Nov. 21, 2000

[54] LIPOSOME ENCAPSULATED AMPHIPHILIC DRUG COMPOSITIONS

[75] Inventors: Frederic Camu, Nieuwerkerken; Mokarram Alafandy, Brussels; Robert Brasseur, Haillot; Franz Legros, Jumet; Oliver Bouffioux, Lesves, all of Belgium

[73] Assignee: Vrije Universiteit Brussel, Brussels, Belgium

[21] Appl. No.: 09/142,260

[22] PCT Filed: Mar. 19, 1997

[86] PCT No.: PCT/EP97/01384

§ 371 Date: Nov. 19, 1998

§ 102(e) Date: Nov. 19, 1998

[87] PCT Pub. No.: WO97/34582

PCT Pub. Date: Sep. 25, 1997

[30] Foreign Application Priority Data

Mar. 21, 1996 [GB] United Kingdom .................. 9605915

[51] Int. Cl.$^7$ .................................................. A61K 9/127
[52] U.S. Cl. .................... 424/450; 424/1.21; 424/9.321; 424/9.51; 424/417; 424/94.3; 264/4.1; 264/4.3
[58] Field of Search .................... 424/450, 1.21, 424/9.321, 9.51, 417, 94.3; 431/829; 935/54; 264/4.1, 4.3, 4.6

[56] References Cited

U.S. PATENT DOCUMENTS 5,244,678 9/1993 Legros et al. .

FOREIGN PATENT DOCUMENTS

| 0 152 379 | 8/1985 | European Pat. Off. . |
|---|---|---|
| 0 233 100 A1 | 8/1987 | European Pat. Off. . |
| 0 317 120 | 5/1989 | European Pat. Off. . |
| 0 488 142 A1 | 6/1992 | European Pat. Off. . |
| 0 152 379 A2 | 8/1995 | European Pat. Off. . |
| 2 592 791 | 7/1987 | France . |
| WO 95/03787 A1 | 2/1995 | WIPO . |

OTHER PUBLICATIONS

J. Boogaerts et al.; ACTA Anaesthesiologica Belgica, vol. 46 No. 1, 19–24 (1995).

G.J. Grant et al., Regional Anesthesia, vol. 19 No. 4, 264–269 (1994).

J.G. Boogaerts et al., British Journal of Anaesthesia, vol. 75 No. 1, 319–325 (1995).

V. Umbrain et al., British Journal of Anaesthesia, vol. 75, 311–318 (1995).

C.J. Grant et al., Anesthesia & Analgesia, vol. 78, S138 (1994).

Primary Examiner—Gollamudi S. Kishore
Attorney, Agent, or Firm—Bacon & Thomas

[57] ABSTRACT

A process for the entrapment of amphiphilic compounds as uncharged or ionic with different mole ratios of phospholipid to the amphiphilic compound. Preparations of ionic species of amphiphilic compounds in the absence of crystals can be prepared, while preparations of uncharged amphiphilic compounds can be prepared with the compound exclusively entrapped inside the liposomes, or partly entrapped inside the liposomes with extraliposomal crystals.

27 Claims, 5 Drawing Sheets

Morphine MP°

Fig. 4 Conformational Analysis of Oxine Insertion into Phospholipid Monolayers

Conformational Analysis of Tin(II)dioxinate into Phospholipid Monolayers

LIPOSOME ENCAPSULATED AMPHIPHILIC DRUG COMPOSITIONS

This application is a 371 of PCT/EP97/01384 filed on Mar. 19, 1997.

The present invention relates to the entrapment of amphiphilic compounds, as uncharged or ionic species, into liposomes, with or without extraliposomal crystals or ions in the suspension; and to a method allowing the prediction of the permeation of these compounds through cell membranes.

Amphiphilic compounds are molecules which possess both a hydrophilic and a hydrophobic part. For example, phospholipids are amphiphilic compounds which comprise two hydrophobic fatty acid chains and a hydrophilic phosphocholine group. In the present invention an example of such compound is tin(II) dioxinate. Amphiphilic compounds may also be represented by uncharged hydrophobic and ionic hydrophilic forms of molecules whose proportions depend upon the pH. The pK of such compounds is defined as the pH at which equal concentrations of both the uncharged and charged forms of the molecule are found. Four such compounds will be specifically described in the present invention, namely morphine, bupivacaine, oxine and clonidine.

STATE OF THE ART
Liposomal Entrapment of Amphiphilic Compounds

Liposomes are vesicles consisting of a double layer of phospholipids in an aqueous solution, with their hydrophilic portions in contact with water and their hydrophobic portions inside the bilayers.

The liposomal encapsulation of amphiphilic compounds into phospholipid mono- and bi-layers has been poorly practised because this type of molecule has generally been considered to be unstable inside phospholipid vesicles (Reference 1).

In order to predict the feasibility and the stability of the association of pharmaceutical compounds with liposomes, the partition coefficient between water and an organic solvent, such as octanol (Poct), has been considered (Reference 1) as is described in Table 1.

TABLE 1

Classification of the behaviour of compounds in liposomes based upon their partition coefficient between water and octanol (Reference 1).

| Log Poctanol | | | | |
|---|---|---|---|---|
| −0.3 | 0 | 1.7 | 4 | 5 |
| Hydrophilic | | Amphiphilic | | Hydrophobic |

Hydrophilic compounds with a negative log octanol/water partition coefficient (Log Poct<−0.3) are entrapped within the inner aqueous compartments of phospholipid vesicles and their stability and release depend upon the respective sizes and the electric charges of the compound and the pores of the lipid layers. Lipid soluble drugs have a high octanol/water partition coefficient (Log Poct>5) and are almost completely trapped inside the lipid layers. Their stability inside the lipid layers may be so high that they are not released anymore from the lipid layers once entrapped (Reference 2). Amphiphilic compounds have an intermediate partition coefficient (−0.3<Log Poct<5) and are readily partitioned between liposomal lipid and water phases depending on the pH of hydration of the vesicles referred to the compound's pK. Amphiphilic compounds were shown to be trapped into the liposomal bilayers only if they formed a complex with the lipid layers acyl chains (Reference 3).

The partition coefficients of most pharmaceutical compounds are within the −0.3 to 5 logarithmic range, thus being amphiphilic (Reference 4). This classification only offers empirical and often erroneous information on their liposomal encapsulation, thereby restricting their currently developed entrapment processes. Indeed, as a consequence of using the partition coefficient of the neutral species as the unique predictive data, amphiphilic compounds have been entrapped into liposomes after insertion of the sole neutral, apolar, hydrophobic species into the preliposomal lipid film. This method has been claimed in several patents or patent applications (References 5 to 9). No entrapment assays into the phospholipid bilayers have been performed using the ionic species of amphiphilic compounds inserted into the preliposomal lipid film, these species being considered as hydrophilic since they are water soluble, and thus unable to be inserted into phospholipid layers (Reference 4). The ionic hydrosoluble species have thus been strictly encapsulated into the intraliposomal aqueous compartment(s) (References 1, 10) as all hydrophilic compounds, the rules being that only "Lipid-soluble compounds may be incorporated within the liposomes by inclusion in the phospholipid mixture during dispersion", while "water-soluble compounds may be entrapped within the liposomes by inclusion in the aqueous medium during dispersion of the phospholipids" (Reference 10). Such has been the case for most amphiphilic compounds, specifically cationic local anaesthetics, including procaine (Reference 11), lidocaine (Reference 12), bupivacaine (Reference 13), and cationic analgesics, including morphine (Reference 14), fentanyl (Reference 15) and alfentanil (Reference 16).

For all of the cases discussed above, the stability of compound entrapment is higher in multilamellar vesicles (MLVs) than in small unilamellar vesicles (SUVs). In addition, MLVs are the simplest liposomes to prepare. A dry lipid film is obtained by evaporation under a nitrogen atmosphere of the organic solvent in which the lipids are dissolved, and then hydrated under agitation. Multilamellar vesicles are thus generally preferred for drug delivery.

The expected improvements of the association of a drug with lipid layers are to increase the therapeutic efficacy, to prolong the duration of action, to reduce the toxicity and side effects, and thus to increase the drug therapeutic index for human clinical application. These improvements are generated by the slow rate of release of the encapsulated drug from the lipid layers. Among the many amphiphilic pharmaceutical compounds, promising animal or effective human results have only been obtained with actinomycin D (Reference 1), vinblastine (Reference 1) and bupivacaine (References 17 to 19).

Pharmaceutical compositions comprising bupivacaine encapsulated in liposomes are described in U.S. Pat. No. 5,244,678 (Reference 8). The compositions which are described are in an injectable form. The encapsulation of bupivacaine in the liposomes is advantageous in that it leads to a superior anaesthetic action as compared to the non-encapsulated drug, to a longer lasting action at equal dosages and to the possibility of reducing the doses to achieve the same or a similar effect (References 18 to 20) The maximum molar ratio of lipid to bupivacaine in the liposomal preparations as described in U.S. Pat. No. 5,244,678 (Reference 8) was about 1.5:1. As mentioned previously with regard to entrapment of lipophilic species of amphiphilic compounds into phospholipid bilayers, the liposomes are obtained by involving uncharged hydrophobic bupivacaine in the phospholipid/cholesterol lipid film and by hydrating at pH 8.1, the pKa of the drug (References 6, 8, 11). These liposomal formulations are saturated with bupivacaine, which forms crystals both inside and outside the liposomes as can been seen by light and electron microscopy (References 17 to 20). Although showing no neurohistopathologic toxicity (References 21,22) and being clinically efficient (References 17 to 19), these formulations are not identical to clinical bupivacaine because of the alkaline pH of the solution, while bupivacaine is currently administered as a cation at acid pH 6.5. Crystals of local anaesthetic are present in the suspensions inside and outside the vesicles. That is the reason why this formulation obtained from U.S. Pat. No. 5,244,678 has been named "Liposome-Associated Bupivacaine" (References 17 to 20).

We have now found that improved liposomal encapsulates bupivacaine compositions, with the whole bupivacaine load entrapped in the liposomes, without bupivacaine crystals in the suspension, can be prepared from lipid films containing lipophilic uncharged bupivacaine. We have also found that other amphiphilic uncharged drug molecules, such as morphine, can be encapsulated in liposomes following similar insertion of uncharged morphine into the preliposomal lipid film and without morphine crystals inside the liposomal suspension. In addition, we have invented a process for entrapping water-soluble ionic amphiphilic compounds into the liposomal bilayers.

SUMMARY OF THE INVENTION

Accordingly, in one aspect the present invention provides a process for preparing multilamellar liposomes and incorporating within the phospholipid bilayers ionic species of amphiphilic compounds comprising a hydrophilic and a hydrophobic portion, which method comprises the steps of:

i) extracting the hydrophilic ionic species from an aqueous medium by an organic solvent in which the phospholipid is dissolved;

ii) preparing a lipid film comprising the phospholipid and the amphiphilic compound by the evaporation to dryness of this solution; and iii) preparing a suspension of multilamellar liposomes by hydration of the lipid film at an acidic pH in the range of from 4 and to 6.5, in such a way that the amphiphilic compound is at least partly inserted into the phospholipid layer beneath the fatty acid $C_2$–$C_3$ hydrophilic interface.

In a second aspect the present invention provides a process for preparing multilamellar liposomes and incorporating within the phospholipid bilayers uncharged amphiphilic compounds comprising a hydrophilic and a hydrophobic portion, which method comprises the steps of a) dissolving the apolar hydrophobic species of the amphiphilic compound in the phospholipid bilayers using predetermined phospholipid/compound mole ratios to obtain preparations of liposomes with the compound exclusively entrapped inside the liposomes without crystals of the compound, or is partly entrapped inside the liposomes with extraliposomal crystals;

b) preparing a lipid film comprising the phospholipid and the amphiphilic compound by the evaporation to dryness of this solution; and c) preparing a suspension of multilamellar liposomes by hydration of the lipid film at a pH at which the amphiphilic compound remains in the uncharged form, in such a way that the amphiphilic compound is at least partly inserted into the phospholipid layer beneath the fatty acid $C_2$–$C_3$ hydrophilic interface.

Figure 1:
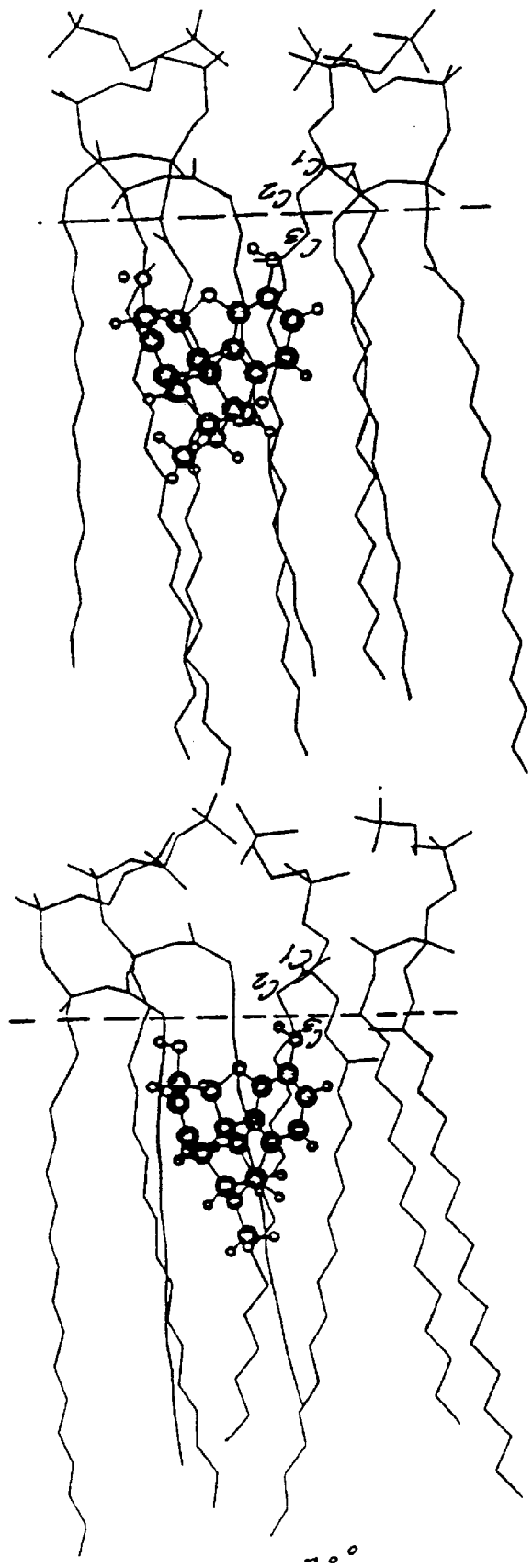
FIGS. 1A and B are schematic representations of the conformational analysis of morphine insertion into phospholipid monolayers.

"Most drugs are weak acids or bases that are present in solution as both the non-ionized and ionized species, and they must pass membrane barriers by diffusion through the bilayer. The non-ionized molecules are usually lipid soluble and can diffuse across the cell membrane. In contrast, the ionized fraction is usually unable to penetrate the lipid membrane because of its low lipid solubility" (Reference 4, p. 4). "Only the non-ionized moiety can readily penetrate the membrane; hence, it diffuses along its concentration gradient until, at steady state, its concentration is the same in both compartments" (Reference 4, p. 4).

These rules often appear contradictory with the physiologic and pharmacologic conditions. Most drugs are formulated as ionic species soluble in an aqueous excipient. Such is the case for all the local anaesthetics, for morphine and opioids. When administered in vivo, they are injected into body fluids which as a rule possess a narrow pH range, from 7.2 to 7.4. At those pHs, most molecules, including local anaesthetics, morphine and opioids, are mainly found in the ionic form which has been claimed as unable to cross the cell membrane. In addition, one fraction of the molecules, depending on the pK(s) of the compound, will be in the hydrophobic apolar form which can thus precipitate as crystals in the body fluids following its hydrosolubility (Table II).

Because of the stated restrictions regarding cell membrane permeation, current high throughput screening of new potential drugs obtained from combinatorial chemistry only focuses on compounds binding to cell membrane receptors.

This screening is performed in vitro by studying the agonist or antagonist relationships of pharmaceutical candidates with isolated receptors. In the current practice, such a screening dramatically restricts new drug discoveries to molecules acting through receptor binding, while most drugs need to penetrate the cell membrane in order to exert their cytoplasmic action (Reference 4). In addition, this screening is completely unaware of the drug's bioavailability involving diffusion between body compartments, absorption, biotransformation in specialized cells (such as hepatocytes) and excretion, which all involve passage across cell membranes (Reference 4) without the involvement of membrane receptors.

TABLE II

Log Poct and pKs of local anaesthetics, morphine and opioids.

| Compound | Log Poct | pKs |
|---|---|---|
| Procaine | −1.7 | 9.05 |
| Chlorprocaine | −0.8 | 8.97 |
| Tetracaine | 0.6 | 8.46 |
| Prilocaine | −0.05 | 7.9 |
| Mepivacaine | −0.1 | 7.76 |
| Lidocaine | 0.5 | 7.91 |
| Bupivacaine | 1.4 | 8.16 |
| Etidocaine | 2.1 | 7.7 |
| Morphine | 0.4 | 7.9 |
| Meperidine | 1.3 | 8.7 |
| Methadone | 2.1 | 9.3 |
| Alfentanil | 2.1 | 6.5 |
| Fentanyl | 3 | 8.4 |
| Sufentanil | 3.2 | 8.1 |

We have demonstrated that the insertion of an amphiphilic compound inside a phospholipid bilayer and the rate of release therefrom do not depend on the partition coefficient but on the stability inside the phospholipid bilayer. Liposomes and phospholipid layers are considered as cell membrane models. The combination of a numeric molecular modelling conformational analysis program and of liposomal entrapment and release assays enable the prediction of the permeability of a biological membrane to a small pharmaceutical molecule. The invention thus offers the screening of a new compound for the permeation of cell membranes leading to cytoplasmic pharmaceutical effects, biotransformation and excretion.

Accordingly, in a further aspect the present invention provides a process for determining the permeation of a cell membrane by an amphiphilic compound as an uncharged or ionic species, which process comprises predicting the mode of insertion into and the stability of the compound in phospholipid monolayers by conformational analysis numeric molecular modelling, preparing multilamellar liposomes incorporating the said amphiphilic compounds according to a process as defined above and determining the release rate of the said amphiphilic compound into a continuously removed buffer solution at pH 7.4.

Conformational Analysis Numeric Molecular Modeling

Numeric molecular modelling is a current major aid in the discovery of pharmaceutically acceptable novel compounds, or families of novel compounds (Reference 23). A numeric molecular modelling program, Theoretical Analysis of Membrane Molecular Organization, TAMMO (Reference 24) has been developed which is able to predict:

1) the hydrophobic/hydrophilic balance of the amphiphilic molecule ($\Phi$), defined as the log of the ratio of the hydrophobic and hydrophilic transfer energies from an apolar to a polar phase;

2) the mode of insertion, the stability and the localisation of the compound inside the bilayers, specifically regarding the hydrophilic/hydrophobic interface of these layers; and 3) the mean interaction energy between one molecule and its surrounding lipids referred to as the energy of insertion of the compound (Reference 24). This energy of interaction between the compound molecular species and the fatty acid chains of the phospholipids is obtained after defining the hydrophobicity potential of the compound showing its hydrophobic and hydrophilic regions calculated taking into account the transfer energy of each atom.

The conformational analysis procedure starts from the HYPERCHEM program (Autodesk, U.S.A.) which optimizes the molecular physico-chemical data in order that the molecule is seen as a volume structure, pointing out the torsions and tensions inside the three dimensional structure. A geometric optimization, performed following the molecular mechanic theoretical data, provides preliminary information leading to a molecular configuration following quantum mechanics. This procedure provides a space configuration taking into account the valence electrons in the optimization process, the internal electrons being included in the nonpolar core of the atom.

From the data of HYPERCHEM, the WinMGM software (Reference 25) enables the hydrophilic and hydrophobic parts of the molecule to be identified and distinguished. Finally, the TAMMO program (Reference 24) predicts the insertion of the compound into phospholipid monolayers, as well as the relationship of the compound with the liposomal cholesterol.

The TAMMO data concerning morphine, bupivacaine, tin(II) dioxinate, oxine and clonidine are summarized in Table III wherein they are also compared with the experimental chemical and morphological results of the liposomal entrapment listed in the following examples and to the log Poct according to the current classification (Reference 1). The current TAMMO program uses dipalmitoyl phosphatidylcholine (DPPC) as the phospholipid molecule assembled into a monolayer.

TABLE III

TAMMO and experimental data

| Compound | Energy -kcal mol$^{-1}$ | PL/X | $\Phi$ | $\Delta$ (A°) | AE % | Release (hours) | Phases(s) | Log Poct |
|---|---|---|---|---|---|---|---|---|
| Morphine | | | | | | | | 0.36 |
| MP° | 33.8 | 4 | 0.5 | 2.36 | 100 | | Hydrophobic/Hydrophilic | |
| | | 10 | | | 91 | 48 | | |
| | | 26 | | | 78 | 30 | | |
| | | 52 | | | 36 | 24 | | |

TABLE III-continued

TAMMO and experimental data

| Compound | Energy -kcal mol$^{-1}$ | PL/X | Φ | Δ (A°) | AE % | Release (hours) | Phases(s) | Log Poct |
|---|---|---|---|---|---|---|---|---|
| MP$^+$ | 23.8 | 4 | 0.46 | 1.90 | | | Hydrophobic/Hydrophilic | |
| Bupivacaine | | | | | | | | 3.6 |
| BP$^0$ | 30.74 | 5 | 0.68 | 0.54 | 80–90 | 24–48 | Hydrophobic/Hydrophilic | |
| BP$^+$ | 30.63 | 5 | 0.63 | 0.69 | 75 | 72 | Hydrophobic | |
| Tin (II) dioxinate | | | | | | | | |
| SnOx$_2$ | 12,31 | 6 | 0.19 | 1.53 | 30 | >72 | | |
| Clonidine | | | | | | | | 1.59 |
| CL$^0$ | 3.1 | 5 | <0 | 0.81 | 14.5 | 0.5 | Hydrophilic | |
| CL$^+$ | 4.3 | 4 | <0 | 0.97 | | | Hydrophilic | |

Legend: PL/X: molar ratio phospholipid to compound; Φ log of the ratio of the hydrophobic and hydrophilic transfer energies from an apolar to a polar phase; Δ: distance between the hydrophobic and hydrophilic centres of the molecule; AE: encapsulation efficiency.

DETAILED DESCRIPTION OF THE INVENTION

The liposomal suspension of the multilamellar vesicles is prepared by hydration of a lipid film comprising the amphiphilic drug encapsulated in polar or ionic form in a phospholipid, optionally in combination with a sterol component. The molar ratio of the phospholipid to the sterol component is preferably in the range of from 1.0 to 1:1, more preferably about 4:3. The phospholipid is preferably, but not exclusively, a L-α- or L-β-phosphatidyl choline (PC), or a mixture thereof, for example egg yolk phosphatidyl choline. The sterol component is preferably cholesterol.

In the present invention, the formation of the preliposomal lipid film is carried out by dissolving the phospholipid, the sterol and the amphiphilic compound in uncharged or in ionic form, in an organic solvent and evaporating the solvent preferably under a nitrogen atmosphere:

Apolar hydrophobic or hydrophilic amphiphilic compounds are thereby inserted into the lipid film. The encapsulation of an uncharged amphiphilic compound occurs through dissolving phospholipid(s) and cholesterol in an organic solvent, adding the uncharged compound in such an amount that the phospholipid/compound (PL/Compound) ratio is higher or lower than the mole ratio corresponding to the saturation of phospholipid molecules by the compound, and hydrating at a pH, preferably alkaline, which ensures that at least 50% of the compound is uncharged. Depending on the phospholipid/compound mole ratio inside the lipid film, the formulation includes:

compound molecules inside the liposomes and crystals in the extraliposomal suspension (PL/Compound ratio<saturation ratio); compound molecules exclusively entrapped inside the liposomes (PL/Compound ratio>saturation ratio).

The incorporation of the hydrosoluble ionic form of an amphiphilic compound occurs through extraction from an aqueous medium using an organic solvent enriched in phospholipid(s), evaporation of the organic solvent, drying to obtain a lipid film including phospholipid(s) and the ionic amphiphilic compound, and hydration at a pH selected to maintain the compound in the ionic form, preferably at an acid pH in the range of from 4 to 6.5.

From the dry lipid film the liposomes are generally formed as suspensions of MLVs in a buffer, for example an isotonic phosphate buffer at pH's from 6.5 to 9. Amphiphilic compounds which may be encapsulated in the liposomes in accordance with the present invention may be anaesthetics, for example, bupivacaine, ropivacaine, prilocaine, mepivacaine, tetracaine or etidocaine, or narcotic analgesic agents such as morphine, fentanyl, alfentanil or sufentanil, and more generally amphiphilic compounds endowed with one pK between pH 3.5 and 10.5, which are the pH limits of pharmaceutical solutions for injection to humans, with at least a part of the molecule inserted under the phospholipid layer hydrophilic/hydrophobic interface of DPPC following the TAMMO program of the conformational analysis methodology.

When the ionic form of an amphiphilic compound is encapsulated in accordance with the present invention it is preferred that the pH of hydration in step (iii) and the pH of the extraction in step (i) are the same, i.e. both within the pH range of from 4 to 6.5.

For the entrapment of bupivacaine in cationic form the phospholipid/bupivacaine mole ratio must be at least 13 in order to avoid the formation of crystals. For the entrapment of morphine in cationic form the phospholipid/bupivacaine mole ratio is at least 20 in order to avoid the formation of crystals. For the entrapment of tin (II) dioxinate in ionic form the phospholipid/tin (II) dioxinate mole ratio is preferably at least 15.

When the uncharged form of an amphiphilic compound is encapsulated in accordance with the present invention, the lipid form from step (b) of the method will be hydrated in step (c) at a pH at which the amphiphilic compound remains in uncharged form, preferably at a pH of about 8.1. In this aspect of the invention compositions are obtained in which the amphiphilic compound is exclusively entrapped inside the liposomes without crystals of the compound, or is partly entrapped within the liposomes with extraliposomal crystals, but no intrapliposomal crystals. The particular molar ratios at which these types of compositions will be formed can be predetermined by progressively increasing the phospholipid/compound mole ratio, hydrating the films as multilamellar vesicles suspensions and determining the presence of or the absence of extraliposomal crystals or intraliposomal crystals by light and/or electron microscopy.

When the uncharged amphiphilic compound is bupivacaine, at a mole ratio of phospholipid/bupivacaine of lower than 13, the bupivacaine is partly entrapped inside the phopsholipid bilayers with entraliposomal crystals. The formation of intraliposomal crystals is avoided at a mole ratio of about 6. At a mole ratio of above 13 the bupivacaine is entrapped in the phopsholipid bilayers in the absence of extraliposomal crystals.

When the uncharged amphiphilic compound is morphine, at a mole ratio of phospholipid/morphine of lower than 20, the morphine is partly entrapped inside the phospholipid bilayers with extraliposomal crystals. At a mole ratio of above 20, generally in the range of from 20 to 40, the morphine is entrapped in the phospholipid bilayers in the absence of extraliposomal morphine crystals.

The present invention includes within its scope the pharmaceutical compositions comprising multilamellar liposomes associated with an amphiphilic compound which have been prepared by the process as described above, in particular such compositions which are in injectable form. The present invention also enables the prediction of an amphiphilic compounds' cell membrane permeation as uncharged and ionic species to be applied in high-throughput screening.

The present invention will be further described with reference to the following Examples.

EXAMPLE 1

Morphine 1.1. Tammo Program Predictions of the Insertion of Morphine Into Phospholipid Monolayers Morphine is an opioid analgesic endowed with a slow onset of effect and a long duration of action (+12 hours) and is currently administered intramuscularly, epidurally or intrathecally (Reference 26). Morphine is used in the treatment of post-operative pain and in cancer pain management. Its side effects may be lethal, leading to respiratory depression. Repeated administrations may induce drug addiction.

Morphine is endowed with two pKs, namely $pK_1=7.93$ and $pK_2=9.63$. This means that it can exist as a cationic, an anionic or an uncharged species. At physiological pH, two forms are prominent, namely apolar morphine ($MP^0$) and its cationic species ($MP^+$). It is poorly soluble in water ($7 \times 10^{-4}$M) when uncharged and soluble in water as $MP^+$ (0.18 M). The uncharged form is poorly soluble in chloroform ($2.0 \times 10^{-4}$M) and the cationic form totally insoluble. The log of the partition coefficient between water and octanol is 0.36 and is thus located in the zone of uncertainty for amphiphilic compound liposomal encapsulation (Reference 1).

The hydrophilic portion of uncharged morphine $MP^+$ is limited to the three oxygen and the nitrogen atoms within the molecule. Accordingly, this hydrophilic portion of the molecule will orient towards the polar headgroups of phospholipid monolayers when the molecule is associated therewith (FIG. 1A).

Using the TAMMO program (Reference 24), a better stability of $MP^0$ inside the DPPC monolayers might be produced, taking only into account the energy of insertion, that for of $MP^0$ being higher than that for of $MP^+$ (Table III).

The modes of insertion of both $MP^0$ and $MP^+$ into DPPC monolayers predicted by the TAMMO programs are shown in FIGS. 1A and B. It can be seen that the hydrophobic portion of both species ($MP^0$, FIG. 1A; $MP^+$, FIG. 1B) lies beneath the interface of the hydrophilic/hydrophobic layers. $MP^+$ is however inserted more deeply into the hydrophobic phase (FIG. 1B). The positioning inside the monolayers leads to the prediction of a higher stability of liposomal entrapment of $MP^+$ than of $MP^0$, although the energies of insertions due to the bonds with the phospholipid fatty acid chains are higher for $MP^0$ than for $MP^+$ (Table IV). It is concluded that the prediction of liposomal encapsulation stability implies both the energy of insertion of a compound and its disposal inside the phospholipid layers, specifically relative to the hydrophilic/hydrophobic interface of these layers.

TABLE IV

Morphine : Conformational analysis numerical data

|  | PL/PL | PL/MP⁺ | PL/MP⁰ | PL/Ch |
|---|---|---|---|---|
| DPPC Energy kJ/mol) | 54 | 99 | 141 | 58 |
| CHOLESTEROL Energy kJ/mol) |  | 41.2 | 25 |  |

It can be seen from Table IV that the energies of insertion, i.e. the stability, of the $MP^0$ form was higher than the $MP^+$ form in DPPC monolayers. Both were higher than the interaction energies between two molecules of phospholipids and between one phospholipid molecule and one cholesterol molecule. The low interaction energies between $MP^0$ or $MP^+$ and cholesterol (−25 and −41 kJ/mol, respectively) indicated that the presence of cholesterol in the phospholipid liposomal layers should not interfere with the encapsulation of both morphine species.

1.2. Processes of $MP^0$ Entrapment Into MLVs

Lipids 100 mg, comprising 72 mg egg phosphatidylcholine (EPC) and 28 mg cholesterol (Ch) and uncharged morphine $MP^0$, in $EPC/MP^0$ molar ratios of from 4 to 100 were dissolved in an organic solution, namely chloroform and methanol in a 10:1 ratio. The organic solution was dried under a nitrogen atmosphere, followed by one night in a vacuum. The encapsulation efficiencies are given in the following Table V. The encapsulation efficiencies progressively decreased with increasing $EPC/MP^0$ molar ratio down to about 80% at a 20:1 ratio. Light microscopy observation of the preparations indicated that the presence of crystals decreased progressively, for $EPC/MP^0$ mole ratios increasing from 4 to 18 (Table V). No crystals were observed from $EPC/MP^0$ ratios of 20. It will be understood from the results that liposomal morphine preparations may be prepared, as desired, with high and low levels of drug encapsulated therein, with or without extraliposomal crystals.

TABLE V

| EPC/MP⁰ | MP⁰ (mg/100 mg Lipids) | Encapsulation efficiency (%) | Crystals |
|---|---|---|---|
| 4 | 6.53 | 100 | XXX |
| 5 | 5.23 | 93 | XXX |
| 6 | 4.37 | 91 | XXX |
| 7 | 3.73 | 91 | XXX |
| 8 | 3.27 | 93 | XXX |
| 9 | 2.9 | 92 | XX |
| 10 | 2.61 | 91 | XX |
| 11 | 2.38 | 89 | XX |
| 12 | 2.18 | 89 | XX |
| 13 | 2.01 | 88 | XX |
| 14 | 1.87 | 97 | X |
| 15 | 1.74 | 86 | X |
| 18 | 1.45 | 80 | X |
| 20 | 1.31 | 78 | 0 |
| 25 | 1.05 | 78 | 0 |
| 30 | 0.871 | 71 | 0 |
| 40 | 0.653 | 64 | 0 |
| 50 | 0.52 | 36 | 0 |
| 60 | 0.436 | 33 | 0 |
| 70 | 0.373 | 38 | 0 |

TABLE V-continued

| EPC/MP⁰ | MP⁰ (mg/100 mg Lipids) | Encapsulation efficiency (%) | Crystals |
|---|---|---|---|
| 80 | 0.327 | 40 | 0 |
| 90 | 0.29 | 39 | 0 |
| 100 | 0.261 | 37 | 0 |

Footnote
XXX = few crystals after hydration but increasing on storage
XX = rare crystals
X = exceptionally rare crystals
0 = no crystals An 80% liposome morphine association efficiency was maintained with mole ratios of from 4 to 25. When the mole ratio was 40 or higher, the association efficiency dramatically dropped to 35% and did not vary anymore until a mole ratio of 100. The optimal EPC/MP⁰ mole ratios are considered to be lower than 18 when MP⁰ crystals are required in the clinical preparations, and from 20 to 30 when the absence of such crystals is required.

1.3. MP⁰ Rate of Release From MLVs

Morphine formulations for human trials were prepared in PL/MP⁰ ratios of 10, 26 and 52. As shown in Tables V, a molar ratio of 10 leads to extraliposomal crystals, whilst this is not the case for the two other preparations.

Lipid films of 100 mg (EPC+Cholesterol), encapsulating MP⁰ in the following amounts:

2.614 mg for an EPC/MP⁰ ratio 10, 1 mg for an EPC/MP⁰ ratio 26, 0.5 mg for an EPC/MP⁰ ratio 52, were prepared according to procedure of 1.2 detailed above. The encapsulation efficiencies of 1 ml PBS at pH 8.1, i.e. at about the pK of the molecule, which is compatible with injectable formulations for humans, are detailed in Table V.

Figure 2:
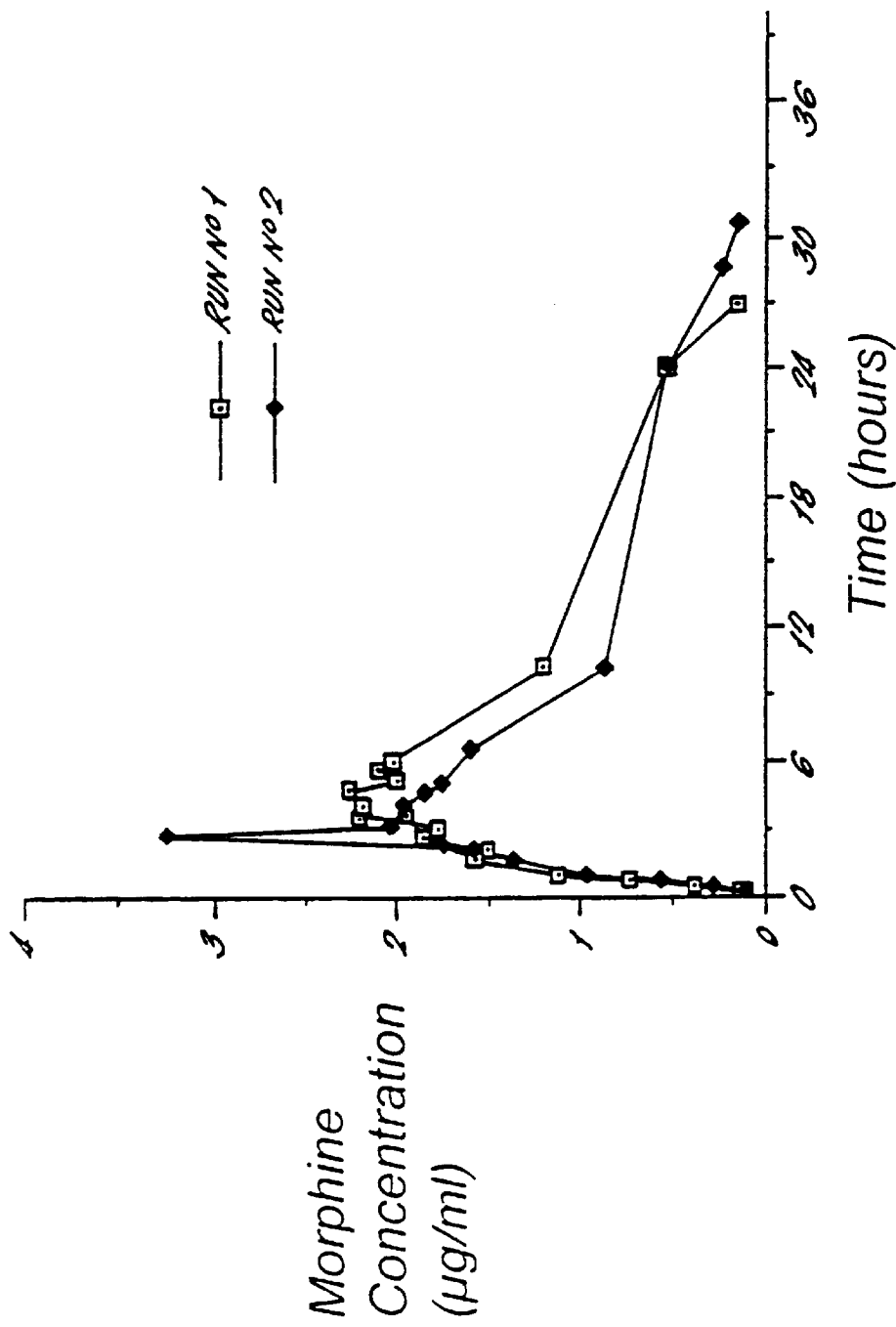
FIG. 2 is a graph of the release of $MP^0$ from liposomes.

The liposomal suspensions were placed in a dialysis bag without centrifugation and immersed in a 150 ml (corresponding to the human cerebrospinal fluid volume) solution of PBS at the physiological pH 7.4, and continuously renewed at the rate of the human cerebrospinal fluid, namely 23 ml per hour. Two preparations were tested under each experimental condition. Morphine was detected in the external medium in the three experiments outlining the liposomal release. FIG. 2 illustrates the release of morphine outside the dialysis bag for two preparations obtained from a PL/MP⁰ ratio of 26 in the lipid film. Peaks of morphine concentrations were observed which were considered to be due to the leakage of free morphine present in the dialysis bag. This peak was rapidly observed, in the hour following the beginning of the release at pH 7.4 in the lipid film EPC/MP⁰ molar ratio 52. It occurred later, between 3 and 6 hours in the 10 and 26 ratios (Ratio 26: FIG. 2). The release was sustained and prolonged in the three experimental conditions. It was limited to 1 day in the 52 ratio formulation and lasted for 30 and 48 hours in the 26 and 10 molar ratios, respectively. It can be concluded that the lower the EPC/MP⁰ molar ratio, the longer the release of the drug from the phospholipid vesicles. The release of MP⁰ from liposomes whatever the EPC/MP⁰ mole ratio confirms the predictions of the TAMMO program concerning the stability of this morphine uncharged species into DPPC monolayers. From the entrapment and release experiments and from the TAMMO predictions, it can be concluded that MP⁰ is able to cross cell membranes.

No crystals were found in the dialysis bag by light microscopy at the end of release for the EPC/MP⁰ ratio 10, indicating that the extraliposomal crystals had been released in the physiological pH 7.4 medium.

1.4. Relationship Between MLV-MP⁰ Formulations and Clinical Requirements

That high encapsulation efficiency, the 30 hour release offer attractive clinical prospects for the EPC/MP⁰ crystal-free formulation at a mole ratio of 26. If longer release times are required in order to obtain longer pain relief, then liposomal formulations with crystals, e.g. a mole ratio of 10, may be prepared. It is concluded that depending on the absence of neuropathological signs, on the admission of crystal formulations for drug administration and on the physicians' coping with associations of morphine entrapped in liposomes and as crystals, the process of liposomal entrapment of this amphiphilic compound as uncharged MP⁰ species described in the present invention (insertion of MP⁰ in the preliposomal lipid film and hydration at alkaline pH favouring the entrapment of MP⁰) offers formulations with high (EPC/MP⁰<25) or low (EPC/MP⁰>40) encapsulation efficiencies presenting a rapid onset of pain relief, with or without crystals depending upon the required duration request of pain relief.

1.5. Entrapment of MP⁺ Into MLVs

One mg MP⁺ was dissolved in 1 ml PBS pH 4.5 (MP⁺ almost 100%). 1 ml chloroform solvent was added. After 24 hours agitation at room temperature, no MP⁺ was found in the organic solvent. When 72 mg (54.9 $\mu$moles) EPC were added to chloroform, corresponding to an EPC/MP⁺ molar ratio of 26, 0.25±0.04 mg MP⁺ was extracted into the lipid phase. The partition coefficient of MP⁺ between water and chloroform with EPC was 0.307, whilst it was 0 in the absence of EPC in chloroform. Accordingly, the presence of phospholipids in organic solvents induces the extraction of the hydrosoluble and lipophilic MP⁺ molecules, thereby confirming the TAMMO prediction that cationic morphine is able to bind to phospholipids. The chloroform/PBS pH 4.5 partition coefficient increased from 0 to 0.307 when EPC was added in the organic phase.

It can be concluded that the extraction of drugs in organic solvents containing dissolved phospholipids is a better indicator of the amphiphilic compounds lipophilicity, defined as the ability to be inserted into phospholipid layers whether in liposomes or in cell membranes. This allows a more precise knowledge of the mode of cell permeation of the drug as a cation at the cell membrane level.

The chloroform+EPC phase was isolated, and 25 mg cholesterol was added in order to obtain an EPC/Cholesterol mole ratio 4:3. The mole ratio EPC/Morphine was 98 in this chloroform phase. Chloroform was evaporated and a dry lipid film was obtained and hydrated by 1 ml PBS pH 4.5 for 24 hours. The encapsulation of cationic morphine was 31.2±2.1% (n=5), corresponding to 0.31 mg±0.02 mg MP⁺ entrapped in the liposomes when referring to the 1 mg MP⁺ initially dissolved in the aqueous medium pH 4.5. The whole MP⁺ extracted in the organic phase (chloroform+EPC) incorporated in the vesicles (0.31 mg±0.02 entrapped in the vesicles from 0.25 mg±0.04 extracted in chloroform+EPC). No MP⁺ was detected in the aqueous phase of the liposomal suspension.

1.6. Release of Morphine From the Liposomal MP⁺ Formulation at pH 7.4

Ten milliters of the MP⁺ liposomal formulation, obtained as described in section 1.5 above, containing 2.8 mg cationic morphine entrapped in 720 mg EPC and 280 mg cholesterol were put in a dialysis bag and immersed in 150 ml PBS at pH 7.4. The PBS medium was continuously renewed at a rate of 23 ml/h at 37° C. The concentration of morphine in the 150 ml PBS was measured over 3 days. The drug concentration in the PBS medium rapidly increased to 6–8 μg/ml in 1 hr, and thereafter sustainedly and slowly decreased over 3 days. This clearly showed that morphine entrapped as $MP^+$ at pH 4.5 was able to be released slowly and according to a concentration gradient from the liposomes, confirming the predictions of the TAMMO program. The clearance time was similar or somewhat longer than that of 2.6 mg apolar morphine entrapped in 72 mg EPC and 28 mg cholesterol and hydrated by 1 ml PBS pH 8.1, leading to a suspension with $MP^0$ crystals (See section 1.3.). These results confirm the predictions of the TAMMO predictions and liposomal encapsulation and release assays, it can be concluded that $MP^+$ is able to cross the cell membranes.

EXAMPLE 2

Bupivacine 2.1. Predictions of Bupivacaine Insertion Into DPPC Monolayers Following the TAMMO Program Bupivacaine is an amphiphilic amino-amide long lasting local anaesthetic. The duration of analgesic action averages 2 to 4 hours following epidural (surgical or obstetrical) or spinal administration, and up to 12 hours in peripheral nerve blocks (References 27, 28). Side effects are motor and sympathetic blocks. Systemic central nervous system and cardiac toxicities have been observed, leading to seizure and cardiac failure. This systemic toxicity becomes apparent at plasma levels averaging 1.6 μg/ml which are close to 1 μg/ml therapeutic concentration. The association with liposomes aims at prolonging the duration of pain relief while avoiding limbs motor blockade and reducing systemic toxicity through slow liposomal release.

Bupivacaine has a pK of 8.16. At this pH 50% of the molecules are cations and 50% are neutral. Acidic solutions are thus enriched with cationic species. Bupivacaine has two hydrophobic portions; one is constituted by the phenyl ring with two methyl groups (xylidine group) on one side and the other by the terminal side aliphatic chain $C_4H_9$ bound to the tertiary nitrogen atom of the other side. The hydrophilic part is around this tertiary central nitrogen atom. The log of the partition coefficient between water and octanol is 1.8, in the range for amphiphilic compounds, based on the partition coefficient (Reference 1).

Using the TAMMO program (Reference 24), the energies of insertion of $BP^0$ and $BP^+$ into DPPC were calculated, as well as the interaction energies between two molecules of DPPC and one molecule of DPPC and one molecule of cholesterol.

The results are given in Table VI.

TABLE VI

Conformational analysis numerical data of bupivacaine : energies of insertion (-kJ/mol) compared with DPPC/DPPC and DPPC/Cholesterol.

| DPPC/DPPC | DPPC/$BP^0$ | DPPC/$BP^+$ | DPPC/Chol |
|---|---|---|---|
| 54.3 | 128.5 | 128 | 58.5 |

It can be seen from this Table that the energies of insertion, i.e. the stability of cationic ($BP^+$) and uncharged bupivacaine ($BP^0$) inserted into DPPC monolayers, are identical and higher than the interaction energies of DPPC/DPPC and DPPC/Cholesterol.

Figure 3:
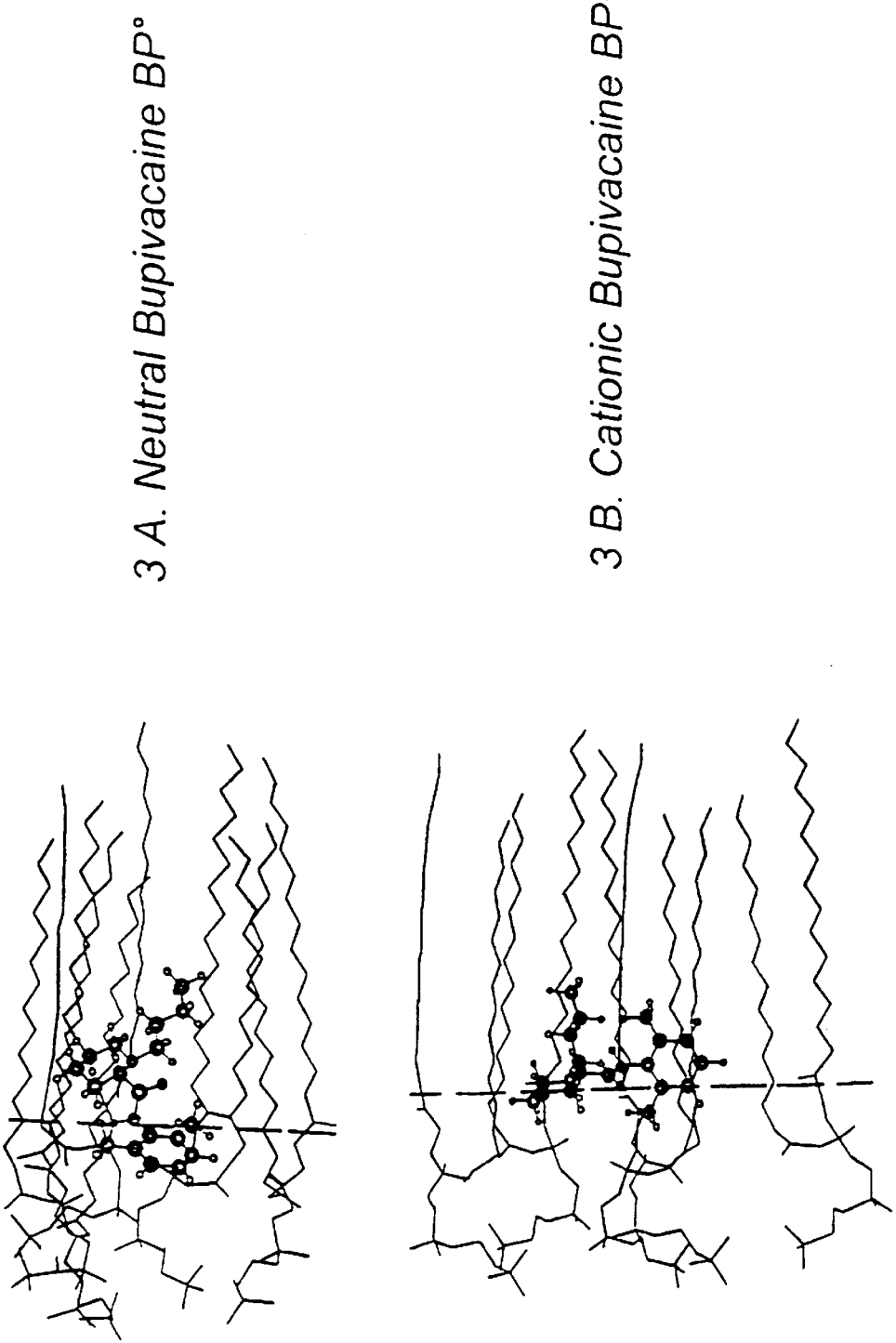
FIGS. 3A and B are a schematic representations of the conformational analysis of bupivacaine insertion into phospholipid monolayers.

The mode of insertion of bupivacaine into a DPPC monolayer drawn from the predictions of the TAMMO program is shown in FIGS. 3A and 3B.

Both bupivacaine species are mainly inserted into the hydrophobic phase of the phospholipid layers, below the carbons $C_2$–$C_3$ of the fatty acids which represents the hydrophobic/hydrophilic interface of the layers.

The TAMMO predictions indicate that the two bupivacaine species offer hydrophobic bonds with the fatty acid chains of the phospholipids assembled in monolayers. The cationic form $BP^+$ offers a straight disposal into the phospholipid layers with hydrophobic bonds at the two ends, both for the hydrophobic xylidine moiety and the $C_4H_9$ groups. The whole molecule lies in the hydrophobic phase of the monolayers, between the $C_2$–$C_3$ interface. The uncharged compound $BP^0$ lies obliquely being in part in the hydrophilic phase above $C_2$–$C_3$ but mainly penetrating into the hydrophobic phase. Both species are thus inserted inside the phospholipid layers at the fatty acid chain level. The position inside the monolayers leads to the prediction of a higher stability of liposomal entrapment of $BP^+$ than of $BP^0$ due to the complete insertion of $BP^+$ into the hydrophobic phase, although the energies of insertion due to the bonds with the phospholipid fatty acid chains are almost equivalent (Table VI). As for morphine, it is concluded that the prediction of liposomal encapsulation stability using a DPPC monolayer implies both the energy of insertion of a compound and its position inside the phospholipid layers, specifically relative to the hydrophilic/hydrophobic interface of these layers.

2.2. Comparison Between the Conformational Analysis Predictions and the Current Hypothesis About Bupivacaine Cell Membrane Permeation These modes of bupivacaine insertion into phospholipid layers are completely different from the current views concerning the molecular relationship between bupivacaine and membrane phospholipid bilayers. According to Covino (Reference 28) "the uncharged base form is important for the optimal penetration of the nerve sheath".

The only active form of local anaesthetic for analgesic action, i.e. the base uncharged form ($BP^0$), would be primarily responsible for diffusion through nerve membranes into axoplasm. This hypothesis is drawn from the liposolubility of the uncharged species given by the octanol/buffer pH 7.4 partition coefficient and agrees with the general overview about compounds' cell membrane permeation limited to the sole uncharged species of an amphiphilic drug (Reference 4). Following the hypothesis based on the partition coefficient in an organic solvent, which currently rules the predictive relations between amphiphilic compounds and phospholipid layers (References 1,4), the ionic species of an amphiphilic compound would be considered unable to insert into phospholipid layers, which is contrary to what has been predicted using the TAMMO program.

2.3. Processes of Entrapment of $BP^0$ Into MLVs

The liposome-associated bupivacaine formulations currently administered to humans (References 17 to 19) are prepared from films of lipids 20 mg (14.4 mg EPC and 5.6 mg Cholesterol) and $BP^0$ varying from 2.5 to 10 mg. These films were hydrated by 1 ml buffer at pH 8.1 and suspended as MLVs with bupivacaine crystals inside and outside the phospholipid vescicles as seen by freeze-etching electron microscopy.

Clinical preparations without crystals can be obtained from EPC/$BP^0$ drug ratio of 13 or above into the lipid film, i.e. at the limit of phospholipid bilayers saturation or above (Table VII). This film was suspended as MLVs in 1 ml buffer pH 8.1. A clinical formulation of bupivacaine 5 mg/ml (0.5%) comprised 231 mg EPC and 90 mg cholesterol associated with 5 mg $BP^0$ and suspended in 1 ml buffer pH 8.1.

When increasing amounts of uncharged $BP^0$ were inserted in a lipid film involving 18.3 μmol EPC (14.4 mg), the presence of bupivacaine crystals was observed in the formulation up to a EPC/BP ratio of 16. No crystals were detected from the ratio 17 and above (Table VII).

It can be concluded that the process of this amphiphilic compound's entrapment as uncharged $BP^0$ offers formulations with or without crystals upon request of pain relief duration and quality.

TABLE VII

| $EPC/BP^0$ Ratio | Crystals |
|---|---|
| 1.25 | ++++ |
| 10 | ++++ |
| 12 | +++ |
| 14 | ++ |
| 16 | + |
| 17 | 0 |
| 20 | 0 |
| 22 | 0 |
| 25 | 0 |

2.4. Release of Bupivacaine From the Liposomal $BP^0$ Formulation at pH 7.4

A first liposomal bupivacaine formulation involved crystals; it was prepared from lipid films made of 14.4 mg EPC, 5.6 mg cholesterol and 5 mg apolar bupivacaine $BP^0$ hydrated by 1 ml PBS at pH 8.1. One milliliter was put in a dialysis bag immersed in 150 ml PBS pH 7.4 at 37° C. continuously renewed at a rate of 23 ml/hr. The release of bupivacaine was measured by HPLC. A maximal concentration (7–8 μg/ml) was attained after 6–12 hours. The whole amount of bupivacaine was released from the liposomes after 2 days.

Under the same experimental conditions the release of bupivacaine from a preparation without crystals, obtained by hydration at pH 8.1 with 1 ml PBS of a lipid film of 230.56 mg EPC, 84.78 mg cholesterol and 5 mg $BP^0$, attained a peak of 5–8 μg/ml after 6 hours, followed by a slow sustained release, and the clearance was complete after 3 days. The release of $BP^0$ from liposomes was thus slower when the liposomal formulation was bupivacaine crystal-free.

2.5. Process of $BP^+$ Entrapment Into MLVs

Cationic bupivacaine 0.5% (5 mg=15.5 μmoles/ml), pH 6.5 was extracted in chloroform with EPC in a molar ratio $EPC/BP^+$ of 6 (i.e. 90 μmoles=70.65 mg EPC). The bupivacaine concentration was measured by UV spectrophotometry at 271.6 nm. After extraction of $BP^+$ in chloroform with EPC, 27.5 mg of cholesterol were added thereto.

After evaporation of the organic solvent under an inert atmosphere and drying of the lipid film, hydration was carried out at pH 6.5. The encapsulation efficiency was measured by UV spectrophotometry at 271.6 nm. It averaged 60±1% after 2 hours and amounted to 74±0.5% after 24 hours. Thus from 5 mg $BP^+$, 3.7 mg were inserted into 70.65 mg MLVs phospholipids.

2.6. Rate of Release of $BP^+$ From MLVs

A further preparation of liposomal $BP^+$ pH 6.5 prepared as described above was inserted into a dialysis bag (5 ml containing 353.25 mg EPC and 25 mg $BP^+$). The bag was immersed in 145 ml PBS pH 7.4 with a renewal rate of 23 ml/hour. Samples of the pH 7.4 medium were harvested at different times and the concentration of bupivacaine was measured by UV spectrophotometry. After a 6 hour rapid transfer of the 25% unencapsulated bupivacaine from the dialysis bag into the physiologic pH medium, a slow release of the liposomal bupivacaine occurred over a period of 3 days.

The extraction of the hydrophilic $BP^+$ in chloroform with EPC the high liposomal encapsulation efficiency of $BP^+$ at pH 6.5, the sustained and prolonged bupivacaine release from the phospholipid vesicles at physiological pH all match the predictions of the TAMMO program concerning the insertion of $BP^+$ into the hydrophobic phase of the phospholipid bilayers from a lipid film involving hydrosoluble but lipophilic $BP^+$, and conform to the concept of lipophilicity through extraction of a compound in an organic solvent containing dissolved EPC. The prolonged 3 day release of liposomal bupivacaine at pH 7.4 suggests a long clinical action of bupivacaine encapsulated as a cation at pH 6.5. In addition, the acidic formulation of $BP^+$ at pH 6.5 is at exactly the same pH as the bupivacaine formulations currently used.

When 1 ml of the same formulation was put in the dialysis bag, the maximal concentration in the 150 ml PBS pH 7.4 was found after 6–12 hours, almost as with the 5 ml described above. A slow and sustained release of $BP^+$ from the liposomes was observed thereafter but it was limited to 24–48 hours.

From those two examples, it can be concluded that the release profile of $BP^+$ is similar to those of the $BP^0$ formulations and does not depend on the amount of liposomal drug put in the dialysis bag: a concentration peak followed by a sustained slow release. But the duration of release was dependent on the liposomal bupivacaine load in the dialysis bag, varying from 3 days for 5 ml of the liposomal formulation to 24–48 hr for 1 ml of the liposomal formulation inside the dialysis bag.

2.7. Conclusions

These encouraging results are in contrast to the state of the art in the matter of cationic bupivacaine liposomal encapsulation and the analgesic results obtained. $BP^+$ has previously been dissolved in an acidic medium and added to a dry lipid film, leading to a primary encapsulation in the liposomal aqueous phase. In those conditions, a prolongation of the sensory block (pain relief) was observed (Reference 13), but accompanied by a motor block (paralysis of the limbs) which outlasted the analgesic action (Reference 29). These pharmacodynamic properties previously led to the encapsulation of $BP^+$ in a liposomal aqueous phase to be rejected. Here again, the combination of the conformational analysis TAMMO program and of liposome entrapment and release assays demonstrates that the cationic species of bupivacaine is able to cross cell membranes, in contrast to the current concept restricting the membrane permeation to the uncharged form of an amphiphilic compound (Reference 4). The combination TAMMO-liposome assays of the present invention thus seems relevant in predicting the behaviour of a small pharmaceutical molecule regarding its cell membrane permeation and may be incorporated as a tool in high-throughput screening complementary to combinatorial chemistry.

EXAMPLE 3

Oxine 3.1. Predictions of the Mode of Insertion of Oxine Into DPPC Monolayers Following the TAMMO Program Oxine (8-hydroxyquinoline) is an amphiphilic molecule presenting two aromatic rings with one nitrogen and one OH. Its pKa is 7.3. It is poorly soluble in water and highly soluble in organic solvents with a partition coefficient octanol/water of 67. The neutral molecule is predominant at the physiologic pH 7.4. But it is also found as a cation at acid pHs and as an anion at basic pHs. Its molecular weight is 186. Oxine is known as a bactericidal agent (Reference 30).

Figure 4:
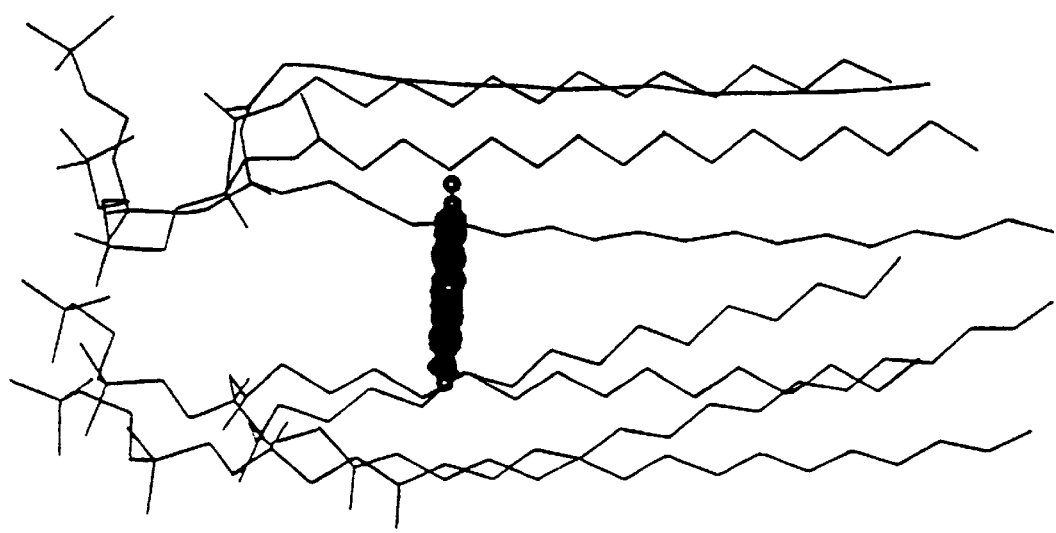
FIG. 4 is a schematic representation of the conformational analysis of oxine insertion into phospholipid monolayers.

The TAMMO program predicted an energy of insertion higher than the relationships between two molecules of DPPC and between DPPC and cholesterol. The mode of insertion of oxine into DPPC monolayers is shown in FIG. 4. The molecule offers hydrophobic bonds between its aromatic rings and the palmitic acid chains on one side, while the hydrophilic OH and nitrogen groups of the compound face the acyl chains of the second DPPC molecule on the other side. This allows the prediction that oxine would be able to be entrapped inside liposomal phospholipid layers, but would be unstable in those layers. This prediction agrees with the intracellular bactericidal mode of action of oxine (Reference 31) after crossing the cell membrane (Reference 32).

3.2. Process of Oxine Entrapment Into MLVs

When 0.7 mg oxine (3.8 $\mu$mol) are mixed with 14.4 mg EPC (18.3 $\mu$mol) and 5.6 mg cholesterol in chloroform, a mol ratio EPC/Oxine of 4.8 was found in the dry lipid film. After hydration by 1 ml PBS pH 7.4, 0.35 mg (50%) was entrapped in the multilamellar vesicles.

3.3. Oxine Release From MLVs

The oxine-MLVs suspension was placed in a dialysis bag which was immersed in 10 ml PBS pH 7.4. The oxine appearing in the medium bathing the dialysis bag was titrated by spectrophotometry at 332 nm. A bulk of the liposomal compound was released in 20 minutes. The release then stopped until the pH 7.4 medium was replaced by a fresh solution, and a new leakage was observed. Such a leakage evokes a movement of the oxine across the liposomal bilayers following a concentration gradient. Oxine is known as a bactericidal agent which acts intracellularly by complexing cytoplasmic metal ions involved in enzymatic reactions. Oxine has been hypothesised to preliminarily cross the bacterial cell membrane following a gradient of concentration (References 30 to 32). The present liposomal release assays confirm this hypothesis and are in agreement with the prediction of the TAMMO program concerning the instability of oxine in DPPC monolayers.

EXAMPLE 4

Tin(II) Dioxinate 4.1. Predictions of the Mode of Insertion of Tin(II) Dioxinate Into DPPC Monolayers Following the TAMMO Program Tin(II) dioxinate ($SnOx_2$) is an amphiphilic compound comprising two molecules of 8-hydroxyquinoline (oxine) bound to a tin(II) atom. It is inserted into liposomes and radiolabelled with 99m-technetium without the additional formation of 99mTc-labelled tin colloids. (References 33, 34).

Tin(II) dioxinate has a hydrophobic moiety comprising the two oxines and a tin(II) hydrophilic part. It is poorly soluble in water, insoluble in ether, ethanol, methanol, octanol, heptane, poorly soluble in chloroform, and moderately soluble in dimethyl sulfoxide (DMSO).

Using the TAMMO program (Reference 24), the energies of insertion of tin(II) dioxinate into DPPC were calculated, as well as the interaction energies between two molecules of DPPC and one molecule of cholesterol (Table VIII).

TABLE VIII

|                              | DPPC/DPPC | DPPC/$SnOX_2$ | DPPC/Ch |
|------------------------------|-----------|---------------|---------|
| Interaction Energy (-kcal/mol) | 13        | 12.3          | 14      |

It can be seen from the Table that the energy of insertion, i.e. the stability of the tin(II) dioxinate inserted into DPPC monolayers, is almost equivalent to the interaction energies of DPPC/DPPC and DPPC/Cholesterol.

Figure 5:
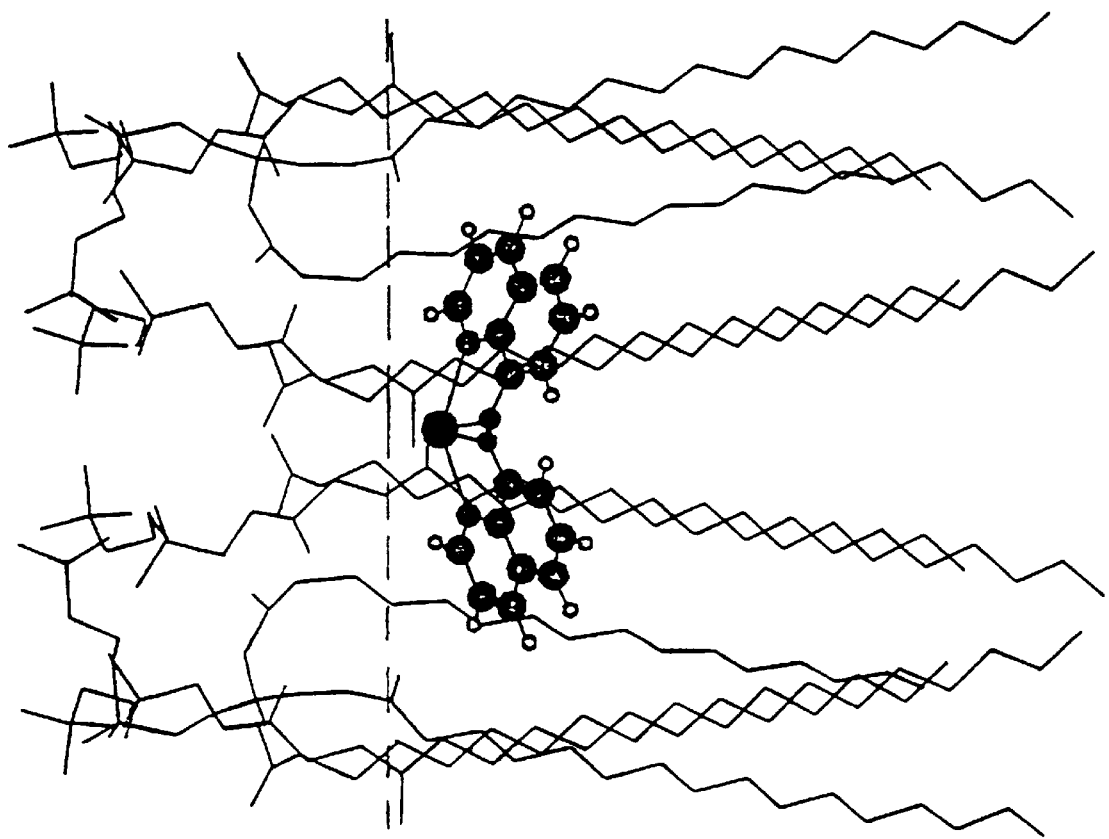
FIG. 5 is a schematic representation of the conformational analysis of tin(II)dioxinate into phospholipid monolayers.
High-Throughput Screening (Reference 23): Predictions of the Permeation of a Small Pharmaceutical Molecule Across Cell Membranes The basic principles of pharmacology state that "the absorption, diffusion, biotransformation, and excretion of a drug all involve its passage across cell membranes. It is essential, therefore, to consider the mechanism by which drugs cross membranes and the physicochemical properties of molecules and membranes that influence this transfer" (Reference 4, p. 3). "When a drug permeates a cell, it must obviously traverse the cellular plasma membrane" (Reference 4, p. 3). "Drugs cross membranes either by a passive process or by a mechanism involving the active participation of components of the membrane. In the former, the drug molecule usually penetrates by passive diffusion along a concentration gradient by virtue of its solubility in the lipid bilayer. Such transfer is directly proportional to the magnitude of the concentration gradient across the membrane and the lipid:water partition coefficient of the drug. The greater the partition coefficient, the higher is the concentration of drug in the membrane and the faster is its diffusion" (Reference 4, p. 4).

The mode of insertion of tin(II) dioxinate drawn from the predictions of the TAMMO program is shown in FIG. 5.

This TAMMO prediction indicates that the whole oxinate molecule, including the "hydrophilic" tin(II) cation interacts with the fatty acid chains inside the hydrophobic phase of the phospholipid layers. The compound occupies the whole space between two adjacent phospholipid molecules. The Tin(II) ion merges into the hydrophilic phase which accounts for its oxido-reduction reaction with $^{99m}TcO_4$ added in the suspension (References 33, 34). Although the energy of insertion is of the order of DPPC/DPPC the insertion of the two oxine moieties into the hydrophobic phase allows the prediction of high stability of the molecules. This prediction agrees with the correlation between the lack of bactericidal activity of dioxinate metal(II) and its unability to cross the cell membranes (References 31, 32).

This mode of tin(II) dioxinate insertion into phospholipid layers is completely different from the three types of metal dioxinate relationships with liposomal phospholipids hypothesized by Hwang (Reference 35). According to this reference no deep bonds are predicted between the oxinate molecules and the inner hydrophobic fatty acid chains of the phospholipid layers. It can be implied from Hwang that the dioxinate groups of the compounds would be unable to insert into the hydrophobic phase of the phospholipid layers, i.e. The fatty acid chains. Thus, the relationship of the metal ion to phospholipid layers should be restricted to the hydrophilic polar head groups of the amphiphilic phospholipids.

4.2. Process of Entrapment of Tin(TI) Dioxinate Into MLVs

The partition coefficient chloroform/water (Pchl) of tin(II) dioxinate was enhanced when EPC 18.3 $\mu$moles was dissolved in the organic solvent before extraction of $SnOx_2$, the limit of solubility being increased by 10-fold: from $4 \times 10^{-4}$ M to $4.1 \times 10^{-3}$ M. The molar ratio EPC/$SnOx_2$ was 4.5. These results reinforce the concept of lipophilicity of a drug in an organic solvent containing EPC, as already developed with bupivacaine and morphine.

Egg yolk phosphatidylcholine (14.4 mg, 18.3 $\mu$mol) and cholesterol (5.6 mg, 13.7 $\mu$mol) were dissolved in chloroform with 0.1, 0.2, 0.3, 0.4, 0.5 mg (1.2 $\mu$mol) and 0.6 mg tin(II) dioxinate. After evaporation of the solvent, hydration occurred with NaCl 150 mM 1 ml. The MLVs thus prepared were washed 5 times in order to discard free tin(II) dioxinate.

The number of tin(II) dioxinate molecules inserted into liposomes increased with the number of $SnOx_2$ molecules present in the preliposomal lipid film. Liposomal saturation occurred for a number of moles averaging 1.23 $\mu$moles $SnOx_2$ inserted into 18.3 $\mu$moles EPC (EPC/$SnOx_2$ mole ratio of 15) with an encapsulation efficiency of 30% for MLVs.

The results are in agreement with the experimental data concerning the solubility in chloroform with EPC.

4.3. Release of Tin(II) Dioxinate From MLVs

When the tin(II) dioxinate MLVs were incubated at pH 7.4, no release was measured for at least one week. This indicates a high stability of insertion into the liposomal layers independent of the pH. This can be explained by the total immersion of the compound inside the phospholipid layer hydrophobic phase, with bonds and coordination between the two oxine molecules and the palmitic acid chains predicted by the TAMMO program and the coordination between tin(II) and hydrophobic molecules demonstrated by DMSO-$d_6$ NMR. Although the energy of insertion is equivalent to one of two DPPC molecules and lower than that for bupivacaine and morphine, the multiple bonds of the compound in its whole chemical structure and inside the hydrophobic phase ensure a high stability of encapsulation provided that the EPC/tin(II) dioxinate molar ratio is not higher than the 15 saturating ratio in the lipid film. This indicates that the mode and the energies of insertion are both necessary to predict the stability of the liposomal entrapment of an amphiphilic compound.

The stability of tin(II) dioxinate in MLVs and its absence of release at physiologic pH 7.4 agrees with previous results indicating that the "mother" molecule of the compound, namely oxine, acts as a bactericidal agent by crossing the bacterial cell membrane. In contrast, all metal(II) dioxinates do not exhibit any bactericidal activity because they are unable to cross the bacterial membrane (References 32,33).

Again, the combination of the TAMMO program predictions and of liposome entrapment and release assays confirms previous experiments on bacteria and verifies that an amphiphilic compound, namely tin(II) dioxinate, is unable to cross the cell membrane. This reinforces the use of the present invention in high-throughput screening.

EXAMPLE 5

Clonidine 5.1. Predictions of Clonidine Entrapment Into DPPC Monolayers Following the TAMMO Program Clonidine is an amphiphilic antihypertensive agent (Reference 36). In the 1990s, clonidine started to be used to improve the quality of analgesia. Unfortunately, when administered in the epidural space of humans, the analgesic effect is associated with a 1 day long hypotensive action (Reference 37). The aim of the association of clonidine with liposome carriers would thus be to reduce the hypotensive effect, whilst maintaining and even improving the analgesic action, through a prolonged slow release from the phospholipid vesicles.

Clonidine has a pK of 8.2. It has a hexacyclic hydrophobic part with two chlorine atoms and a hydrophilic pentacyclic part with two nitrogen atoms. It is highly soluble in acidic solution as a cation, and soluble in octanol when uncharged. Its log Poct/buffer at pH 7.4 is 1.59, in the zone of amphiphilic molecules with uncertainty regarding the prediction of liposomal encapsulation based on partition coefficients (Reference 1).

The numerical data concerning the energies of association of uncharged ($CL^0$) and cationic ($CL^+$) clonidine species with DPPC monolayers predicted by the TAMMO program are illustrated in Tables III and IX.

TABLE IX

TAMMO numerical data of clonidine insertion into DPPC monolayers. Interaction energies of both clonidine species compared with DPPC/DPPC and DPPC/Cholesterol.

|  | DPPC/DPPC | DPPC/$CL^+$ | DPPC/$CL^0$ | DPPC/Ch |
|---|---|---|---|---|
| Energy (-kal/mol) | 13 | 4.3 | 3.1 | 14 |

The energies of insertion of both $CL^0$ and $CL^+$ are lower than those between two molecules of DPPC or DPPC and cholesterol. The stability of both clonidine species inside phospholipid vesicles can thus be predicted as being too low to ensure the stability of the compound inside the fatty acid lipid phase monolayers.

In contrast to the predictions of the TAMMO program concerning morphine, bupivacaine and tin(II) dioxinate, both $CL^0$ and $CL^+$ species are bound to the end of the phospolipid fatty acid chains through their hydrophobic part, close to the hydrophilic polar phosphocholine head groups, and close to ($CL^0$) or inside ($CL^+$) the hydrophilic phase above the $C_2$–$C_3$ interface. The $CL^+$ proton interacts with a phosphate group of the polar head, whilst the phenyl group interacts with the first carbon of the fatty acid chains in both species.

5.2. Process for Encapsulation of Clonidine Into MLVs

The liposomal encapsulation of clonidine was measured by U.V. spectrophotometry at 271 nm. Lipid films at 14.4 mg EPC (18.3 μmoles), 5.6 mg Ch and 0.5 mg $CL^0$ (2.2 μmoles) were hydrated by 1 ml isotonic buffer pH 7.8 (71.5% $CL^+$; 28.5% $CL^0$). The encapsulation efficiency was:

14.5%±0.4% (n=6); or 72.5 ug/ml±2 μg/ml; or 0.315±0.008 μmoles.

The encapsulation efficiency was thus significantly and reproducibly low.

5.3. Release of Clonidine From MLVs

The release of encapsulated clonidine was measured at pH 7.4 after 1, 3 and 6 hours. Almost all the liposomal compound leaked out of the phospholipid vesicles after 1 hour. The low clonidine encapsulation level and its rapid release are in close agreement with the TAMMO predictions and thus liposomes cannot be considered to be useful carriers of the compound, whether in the $CL^0$ or $CL^+$ form.

Evaluation

Liposomal entrapment of amphiphilic compounds. From the results summarized in Table II, it appears that amphiphilic molecules inserted into the hydrophobic phase (beneath carbons $C_2$–$C_3$ of the fatty acid chains) of the phospholipid layers would be preferably encapsulated into liposomes, from lipid films made of phospholipids, cholesterol and the amphiphilic compound as an uncharged or ionic species. These criteria give precise information concerning the liposomal encapsulation of an amphiphilic compound. In contrast the log Poct is irrelevant, since the partition of clonidine which is poorly insertable and unstable into phospholipid vesicles is higher than that of morphine which is highly encapsulated, stable and releasable at physiological pH. Considering the poor stability in water and in organic solvents, specifically the insolubility in octanol, no predictions can be made concerning the liposomal encapsulation of tin(II) dioxinate based upon the log Poct. TAMMO predictions, confirmed by experimental data, allow tin(II) dioxinate to be defined as an amphiphilic compound when considering its insertion into liposomal phospholipid bilayers.

The present invention thus allows the prediction the mode of insertion and therefrom the stability of an amphiphilic compound, as uncharged or ionic species, into a phospholipid layer. These predictions in turn enable the feasibility of the two species of an amphiphilic compound liposomal entrapment to be decided. They also allow the prediction of whether or not a compound will permeate the cell membrane.

High-Throughput Screening

Most pharmaceutical small molecules are known to act or to be metabolised intracellularly after crossing the cell membrane (Reference 4). The examples above have demonstrated that the partition in organic solvents, specifically octanol, does not offer reliable data about the ability of a compound to be inserted or to cross a phospholipid bilayer, including a cell membrane. In contrast the combination of the predictive TAMMO program molecular modeling and of liposomal entrapment and release assays, which together form the core of the present invention, present a reliable prediction of the ability to cross cell membranes. Billions of new small pharmaceutical molecules are currently being elaborated by computerized combinatorial chemistry. The present combination TAMMO-liposome assay is a computerized and automated experimental tool for predicting the behaviour of small pharmaceutical compounds regarding the permeability of cell membranes.

REFERENCES

1. Betageri G V, Jenkins S A, Parsons D L. Liposome Drug Delivery Systems. Lancaster: Technomic Publishing Co. (1993).
2. Benameur H, Latour N, Schandene L, Van Vooren J P, Flamion B, Legros F J. Liposome-incorporated dexamethasone palmitate inhibits in-vitro lymphocyte response to mitogen. Journal of Pharmacy and Pharmacology 47: 812–817 (1995).
3. Defrise-Quertain F, Châtelain P, Delmette M, Ruschaaert J M. Model studies for drug entrapment in liposomes. Liposome Technology: Incorporation of Drugs, Proteins and Genetic Material. Edited by Gregoriadis G. Boca Raton: CRC Press, 1–17 (1984).
4. Benet L Z, Sheiner L B. Pharmacokinetics: the dynamics of drug absorption, distribution and elimination. In The Pharmacological Basis of Therapeutics. Gilman A G, Goodman L S, Rall T W, Murad F, Eds. McMillan Publishing Cy, New York pp. 4 (1995).
5. Muntwyler R D. Verfahren zur Herstellung von pharmazeutischen Zussammenetzungen enthaltend unilamellare Liposomen. Europaïsche Patentanmeldung, Ciba-Geigy AG, 1984.
6. Legros F, Ruysschaert J M. Composition pharmaceutique, contenant un anesthésique local et/ou un analgésique central encapsulé dans des liposomes. IRE-Celltarg S.A. Demande de brevet européen, 1986.
7. Schmitt J, Nehne J, Feller W and Berger S. Verfahren zur Verkapselung fester oder flüssiger, lipophiler Wirkstoffe zu diesen Wirkstoff enhaltenden Phospholipid-Liposomen sowie Arzneimittel diese Liposomen enthaltend. Europaïsche Patentanmeldung, Braün Melsungen, 1990.
8. Legros F, Ruysschaert J M. Pharmaceutical composition containing a local anesthetic and/or a centrally acting analgesic encapsulated in liposomes. U.S. Pat. No. 5,244,678 A, 1991.
9. Foldvari M. Biphasic multilamellar lipid vesicles. Patent Application, 1994.
10. New RRC. Influence of liposome characteristics on their properties and fate. In Liposomes as Tools in Basic Research and Industry. Philipot J R, Schuber F, Ed. CRC Press, Boca Raton. pp. 8 (1995).
11. Stozek T, Krowezynski L. The effect of entrapment of procaine hydrochloride on liposomes on its local anesthetic action. Pharmazie 44: 466–468 (1989).
12. Mashimo K, Uchida I, Pak M, Shibata A, Nishimura S, Ingaki Y, Yoshida I. Prolongation of canine epidural anesthesia by liposome encapsulation of lidocaine. Anesthesia & Analgesia 74: 827–834 (1992).
13. Grant G J, Vermeulen K, Zakowski M, Langerman L, Stenner M, Turndorf H. Prolonged analgesia and decreased toxicity with liposomal bupivacaine. Anesthesiology 79, A869 (1993).
14. Kim T, Mürolauda S, Grüber A, Kim S. Sustained-release morphine for epidural analgesia in rats. Anesthesiology 85: 351–358 (1996).
15. Hung O R, Whynot S C, Varvel J R, Shafer S L, Mezei M. Pharmacokinetics of inhaled liposome-encapsulated fentanyl. Anesthesiology 83: 277–284 (1995).
16. Bernards C M, Luger T J, Malmberg A B, Hill H F, Yaksh T L. Liposome encapsulation prolongs alfentanil spinal analgesia and alters systemic redistribution in the rat. Anesthesiology 77: 529–535 (1992).
17. Boogaerts J G, Lafont N D, Declercq A G, Luo H C, Gravet E T, Bianchi J A, Legros F J. Epidural administration of liposome-associated bupivacaine for the management of postsurgical pain: a first study. Journal of Clinical Anaesthesia 6: 315–320 (1994).
18. Lafont N D, Boogaerts J G, Legros F J. Use op liposome-associated bupivacaine for the management of a chronic pain syndrome. Anesthesia & Analgesia 79: 818 (1994).
19. Lafont N D, Legros F J, Boogaerts J G. Use of liposome-associated bupivacaine in a cancer pain syndrome. Anaesthesia 51: 578–579 (1996).
20. Boogaerts J G, Lafont N D, Carlino S, Noel E, Raynal P, Goffinet G, Legros F J. Biodistribution of liposome-associated bupivacaine after extradural administration to rabbits. British Journal of Anaesthesia 75: 319–325 (1995).
21. Malinowsky J M, Benhamou D, Mussini J M, Legros F J. Liposomal bupivavaine in the rabbit: neuropathologic study. British Journal of Anaesthesia 74: 73 (1995).
22. Boogaerts J, Lafont N, Donnay M, Luo H, Legros F J. Motor blockade and absence of local nerve toxicity induced by liposomal bupivacaine into the brachial plexus of rabbits. Acta Anaesthesiologica Belgica 46: 19–24 (1995).
23. De Witt S H. Molecular diversity strategies. Pharmaceutical News 1: 11–14 (1994).
24. Brasseur R. TAMMO: Theoretical analysis of membrane molecular organization. Molecular Description of Biological Membranes of Computer Aided Conformational Analysis, Vol. 1 Edited by Brasseur R. Boca Raton: CRC Press, 203–219 (1993).
25. Rahman M, Brasseur R, Win M G M. A fast CPK molecular graphics program for analyzing molecular structure. Journal of Molecular Graphics 12: 212–218 (1994).
26. Cousins M J, Cherry D A, Gourlay G K. Acute and chronic pain: use of spinal opioids. Neural Blockade in Clinical Anesthesia and Management of Pain. Edited by Cousins M J, Bridenbaugh P O, Philadelphia: J P Lippincott, 955–1027 (1988).
27. Covino B G. Clinical pharmacology of local anesthetic agents, Neural Blockade in Clinical Anesthesia and Management of Pain. Edited by Cousins M J, Bridenbaugh P O. Philadelphia: J P Lippincott, 112 (1988).
28. Covino B G. Local anesthetics, Postoperative Pain Management. Edited by Ferrante F M, VadeBoncoeur T R. New York: Churchill Livingstone, 215 (1993).
29. Grant G J, Vermeulen K, Langerman L, Stenner M, Zakowski M, Turndorf H. Liposomal bupivacaine block of the sciatic nerve produces motor paralysis which outlasts analgesia in rats. Anesthesia Analgesia 78: S138 (1994).
30. Albert A, Rubbo S D, Goldacre R J, Balfour B G. The influence of chemical constitution on antibacterial activity. Part III: A study of 8-hydroxyquinoline (oxine) and related compounds. British Journal of Experimental Pathology 28: 69–87 (1947).
31. Albert A, Gibson M I, Rubbo S D. The influence of chemical constitution on antibacterial activity. Part VI:

The bactericidal action of 8-hydroxyquinoline (oxine). British Journal of Experimental Pathology 34: 119–130 (1953).

32. Albert A, Hampton A, Selbie F R, Simon R D. The influence of chemical constitution on antibacterial activity. Part VII: The site of action of 8-hydroxyquinoline (oxine). British Journal of Experimental Pathology 35: 75–84 (1954).

33. Umbrain V, Alafandy M, Bourgeois P, D'Haese J, Boogaerts J G, Goffinet G, Camu F, Legros F J. Biodistribution of liposomes after extradural administration in rodents. British Journal of Anaesthesia 75: 311–318 (1995).

34. Alafandy M, Goffinet G, Umbrain V, D'Haese J, Camu F, Legros F J. $^{99m}$Tc-stannous oxinate as marker of liposome formulations. Nuclear Medicien & Biology, in press.

35. Hwang K J. Modes of interaction of $(In^{3+})$-8-hydroxyquinoline with membrane bilayers. Journal of Nuclear Medicine 19: 1162–1170 (1978).

36. Rudd P, Blaschke T F. Antihypertensive agents and drug therapy of hypertension, The Pharmacological Basis of Therapeutics. Edited by Goodman A G, Goodman L S, Rall T W, Murad F. New York: MacMillan Publishing Cy, 784–805, 1993.

37. Eisenach J, Detweiller D, Hood D. Hemodynamic and analgesic actions of epidurally administered clonidine. Anesthesiology 78: 277–287 (1993).

What is claimed is:

1. A process for preparing multilamellar liposomes and incorporating within the phospholipid bilayers thereof ionic species of amphiphilic compounds comprising a hydrophilic and a hydrophobic portion, which method comprises the steps of:

i) selecting an amphiphilic compound the ionic species of which will at least partly insert into the liposomal phospholipid bilayers by numeric molecular modelling or conformational analysis;

ii) extracting the hydrophilic ionic species of the said amphiphilic compound from an aqueous medium by means of an organic solvent in which the phospholipid is dissolved;

iii) preparing a lipid film comprising the phospholipid and the amphiphilic compound by the evaporation to dryness of this solution; and iv) preparing a suspension of multilamellar liposomes by hydration of the lipid film at an acidic pH in the range of from 4 and to 6.5, whereby the ionic species of the amphiphilic compound is at least partly inserted into the phospholipid layer beneath the fatty acid $C_2$–$C_3$ hydrophilic interface.

2. A process of as claimed in claim 1 wherein the dried lipid film from step (iii) is hydrated at the pH of the aqueous solution in which the amphiphilic ion was first dissolved.

3. A process as claimed in claim 1 wherein the ionic species is cationic bupivacaine, ropivacaine, prilocaine, mepivacaine, tetracaine or etidocaine.

4. A process as claimed in claim 3 wherein the phospholipid/bupivacaine mole ratio is at least 13.

5. A process as claimed in claim 3 wherein the lipid film from step (ii) is hydrated at a buffered pH averaging 6.5.

6. A process as claimed in claim 1 wherein the ionic species is cationic morphine.

7. A process as claimed in claim 6 wherein the phospholipid/morphine mole ratio is at least 20.

8. A process as claimed in claim 6 wherein the lipid from step (ii) is hydrated at a buffered pH averaging 5.

9. A process as claimed in claim 1 wherein the ionic species is tin(II) dioxinate.

10. A process as claimed in claim 9 wherein the phospholipid/tin(II) dioxinate mole ratio is at least 15.

11. A process as claimed in claim 9 wherein the lipid film from step (ii) is hydrated at a buffered pH averaging 6.5.

12. A process for preparing multilamellar liposomes and incorporating within the phospholipid bilayers thereof uncharged amphiphilic compounds comprising a hydrophilic and a hydrophobic portion, which method comprises the steps of a) wherein the molar ratio of the phospholipid/compound at which the compound is exclusively entrapped inside the liposomes without crystals of the compound, or is partly entrapped in the liposomes with extraliposomal crystals, but no intraliposomal crystals, is predetermined by progressively increasing the phospholipid/compound mole ratio, hydrating the films as multilamellar vesicles suspensions and determining the presence of or the absence of extraliposomal crystals or intraliposomal crystals by light and/or electron microscopy;

b) dissolving the apolar hydrophobic species of the amphiphilic compound in the phospholipid bilayers using the predetermined phospholipid/compound mole ratios to obtain preparations of liposomes with the compound exclusively entrapped inside the liposomes without crystals of the compound, or partly entrapped inside the liposomes with extraliposomal crystals;

c) preparing a lipid film comprising the phospholipid and the amphiphilic compound by the evaporation to dryness of this solution; and d) preparing a suspension of multilamellar liposomes by hydration of the lipid film at a pH at which the amphiphilic compound remains in the uncharged form, whereby that the amphiphilic compound is at least partly inserted into the phospholipid layer beneath the phospholipid fatty acid $C_2$–$C_3$ hydrophobic/hydrophilic interface.

13. A process as claimed in claim 12 wherein the uncharged amphiphilic compound is bupivacaine and the phospholipid/bupivacaine mole ratio in the lipid film is lower than 13, whereby the bupivacaine is partly entrapped inside the phospholipid bilayers with extraliposomal crystals.

14. A process as claimed in claim 12 wherein the uncharged amphiphilic compound is bupivacaine and the phospholipid/bupivacaine mole ratio in the lipid film is 13 or higher, whereby the bupivacaine is entrapped in the phospholipid bilayers in the absence of extraliposomal bupivacaine crystals.

15. A process as claimed in claim 12 wherein the uncharged amphiphilic compound is morphine and the phospholipid/morphine mole ratio in the lipid film is lower than 20, whereby the morphine is partly entrapped in side the phospholipid bilayers with extraliposomal morphine crystals.

16. A process as claimed in claim 12 wherein the uncharged amphiphilic compound is morphine and the phospholipid/morphine mole ratio in the lipid film is 20 or above, whereby the morphine is entrapped in the phospholipid bilayers in the absence of extraliposomal morphine crystals.

17. A process as claimed in claim 16 wherein the mole ratio is up to 40.

18. A process as claimed in claim 12 wherein the hydration of the film in step (c) is carried out at a pH of 8.1.

19. A process as claimed in claim 12 wherein the lipid film comprising the phospholipid and amphiphilic compound are hydrated with a buffer or NaCl 0.9% to a final pH in the range of from 3.5 to 10.5, the particular pH range which is selected being compatible for an injectable formulation, and being selected as a function of the pKs of the amphiphilic compound and depending upon whether the desired clinical formulation of the amphiphilic compound is as an uncharged or ionic species.

20. A process as claimed in claim 12 wherein the phospholipid is L-α or L-β phosphatidyl choline, or a mixture thereof.

21. A process claimed in claim 12 wherein the lipid film additionally comprises a sterol.

22. A process as claimed in claim 20 wherein the molar ratio of phospholipid:sterol is in the range of 1.0 to 1:1.

23. A process as claimed in claim 12 wherein the suspensions of multilamellar liposomes are prepared in an injectable form.

24. A pharmaceutical composition which comprises multilamellar liposomes associated with an amphiphilic compound which has been prepared by a process as claimed in claim 12.

25. A pharmaceutical composition as claimed in claim 24 which is an injectable form.

26. A process for determining the permeation of a cell membrane by an amphiphilic compound as an uncharged or ionic species, which process comprises predicting the mode of insertion into and the stability of the compound in phospholipid monolayers by conformational analysis numeric molecular modeling, preparing multilamellar liposomes incorporating the said amphiphilic compounds according to a process as claimed in claim 1, and determining the release rate of the said amphiphilic compound into a continuously renewed buffer medium at pH 7.4.

27. A process as claimed in claim 26 which is used to screen an amphiphilic compound for cell membrane permeation.

* * * * *